United States Patent [19]
Galkin

[11] Patent Number: 6,049,583
[45] Date of Patent: Apr. 11, 2000

[54] METHOD AND APPARATUS FOR MEASURING COMPRESSION FORCE IN MAMMOGRAPHY

[76] Inventor: Benjamin M. Galkin, 35 Ivy La., Cherry Hill, N.J. 08002

[21] Appl. No.: 08/888,985

[22] Filed: Jul. 7, 1997

Related U.S. Application Data

[63] Continuation-in-part of application No. 08/636,423, Apr. 23, 1996, abandoned, which is a continuation-in-part of application No. 08/501,153, Jul. 11, 1995, abandoned, which is a continuation of application No. 08/104,450, Aug. 10, 1993, abandoned.

[51] Int. Cl.[7] ......................................................... A61B 6/04
[52] U.S. Cl. ............................................. 378/37; 378/207
[58] Field of Search ....................................... 378/37, 207

[56] References Cited

U.S. PATENT DOCUMENTS

4,744,099   5/1988   Huettenrauch et al. .................. 378/37

*Primary Examiner*—Craig E. Church
*Attorney, Agent, or Firm*—Woodcock Washburn Kurtz Mackiewicz & Norris LLP

[57] ABSTRACT

Methods and apparatus for testing and recording the performance of mammography compression devices are shown to include compression phantoms to which the compression force is applied and the compression phantom is imaged. The compression phantoms are provided with compression force measurement features for radiographically determining the performance of the mammography compression device in terms of the magnitude of the compression force applied to the compression phantoms. Methods for measuring compression forces of mammography systems using the compression phantoms are described as positioning a compression phantom, equipped with a compression force measurement feature, between a compression paddle and breast support platform of a mammography unit, applying a compression force to the compression phantom with the compression paddle to produce a spatial response of the compression force measurement feature, radiographing the compression phantom to produce a latent image on a film of the compression phantom and spatial response of the compression force measurement feature, processing the film to develop a radiographic image of the compression phantom and the spatial response of the compression force measurement feature, and determining the magnitude of the compression force applied to the compression phantom by comparing the radiographic image of the spatial response of the compression force measurement feature to a calibration pattern. Methods and apparatus described herein are useful for testing mammography compression devices and are particularly useful in providing permanent records of compression performance.

8 Claims, 8 Drawing Sheets

METHOD AND APPARATUS FOR MEASURING COMPRESSION FORCE IN MAMMOGRAPHY

RELATED APPLICATIONS

The present application is a continuation-in-part of application Ser. No. 08/636,423 filed on Apr. 23, 1996, now abandoned, which in turn is a continuation-in-part of application Ser. No. 08/501,153 filed on Jul. 11, 1995, now abandoned, which in turn is a continuation of application Ser. No. 08/104,450 filed on Aug. 10, 1993, now abandoned.

FIELD OF THE INVENTION

This invention relates generally to the field of radiology, and more specifically to methods, apparatus and system for measuring compression force exerted by mammography compression devices used in mammography.

BACKGROUND OF THE INVENTION

Mammography is the process of obtaining x-ray images of the human breast for diagnosis or surgery. It involves positioning a patient's breast on a breast support platform of a mammography unit and exposing the breast to x-rays to create a latent image of the breast on an image receptor. The image receptor is a film, in contact with an intensifying screen that fluoresces when struck by x-rays. The film and intensifying screen are contained in a cassette which is located in a cassette holder directly beneath the breast support platform. After exposure to x-rays, the film is removed from the cassette and developed to produce a radiographic image of the breast.

As is known to those with skill in the art, before the breast is exposed to x-rays, it is compressed against the breast support platform by a mammography compression device. This is done in order to reduce patient radiation dose, patient motion, and scattered radiation to the film, and to increase image contrast and improve image quality.

The mammography compression device consists of a rectangular flat plate, called a compression paddle or a compression plate, that is attached to the mammography unit. The edges of the plate are turned upward away from the breast support platform to provide a smooth edge for the patient. The compression paddle is located between the breast support platform and the x-ray tube of the mammography unit. The plane of the compression paddle is parallel to the breast support platform and perpendicular to the axis of the x-ray beam. The compression paddle is movable along a line parallel to the axis of the x-ray beam. The compression paddle is usually made of thin, plastic that absorbs only a small fraction of the incident x-ray beam.

For clinical use of the mammography compression device, the breast is positioned on the breast support platform in the desired orientation. This is facilitated by a light beam originating from the x-ray tube assembly that passes through the compression paddle and illuminates the area of the breast support platform that will be exposed to x-rays.

The compression paddle is moved either manually or by power drive to apply a compression force to the breast, thus flattening the breast against the breast support platform to a near uniform thickness. An x-ray exposure is then made. After the x-ray exposure the compression force is released and the breast recovers its normal shape.

A complete mammographic study usually involves at least two x-ray exposures of each breast, 1) a cranio-caudad view in which the breast is compressed in a superior-inferior direction, i.e. from the direction of the patient's head downward against the breast lying on the breast support platform. The plane of the breast support platform is parallel to the floor and the x-ray beam is directed vertically downward; and 2) a lateral or oblique view in which the breast is compressed medio-laterally, i.e., from midline sidewise against the breast support platform which is angled, along with the axis of the x-ray ray beam, relative to the floor.

Adequate compression is an important factor in achieving good quality mammograms, and mammography facilities that are accredited by the American College of Radiology (ACR) and certified by the U.S. Food and Drug Administration under the Mammography Quality Standards Act of 1992 (MQSA) are required to test their mammography compression devices periodically. Although there are a number of test tools that can be used (1), the method recommended by the ACR (2), and usually employed, consists of positioning a bathroom type scale on the cassette holder, and applying a compression force to the scale either manually or remotely using the compression paddle attached to the x-ray unit. The final scale reading is recorded manually in a log. The test records are subject to periodic review by authorized MQSA personnel. The breast support platform and compression paddle are protected by towels or foam pads before pressure is applied to the scale.

Other known test tools for measuring the force exerted by mammography compression devices include hydraulic load cells, industrial strain gauges, compression force gauges made of compressible polyethylene packing material, and extension type scales.

Although the bathroom type scale is the most widely used method for testing mammography compression devices there is no standard scale designed expressly for this purpose, and in practice the scales vary considerably in size, shape, weight, sensitivity and accuracy. The aforementioned other prior methods for testing mammography compression devices do not satisfy long-felt needs in the art for methods and apparatus to measure the magnitude of compression force applied by mammography compression devices that are quick, efficient, and standardized to particular types of mammography units.

It is also known in the field of radiology to utilize inanimate objects is place of patients in conducting serial x-ray exposures for calibration, image quality, and dosimetry purposes. Such an object is called a phantom and in mammography the object is called a breast phantom. The inventor of the subject matter herein claimed and disclosed has recognized a long-felt need in the art for an inanimate object designed specifically for testing mammography compression devices. The inventor calls such a device a compression phantom.

It is also well known in the field that bathroom type scales presently used to test mammography compression devices are usually heavy and need to be supported by a chair or other support in order to perform the test when the x-ray beam is angled off the vertical. The inventor of the subject matter herein claimed and disclosed has also recognized additional long-felt needs in the art for methods and apparatus that are light weight and capable of measuring compression force, not only for vertical downward projections of the x-ray beam, but also for lateral and oblique projections.

The inventor of the subject matter herein claimed and disclosed has recognized a need in the art for a compression phantom that can be used with or incorporated into a breast phantom for testing mammography image quality.

The inventor of the subject matter herein claimed and disclosed has recognized further long-felt needs in the art for methods and apparatus to measure the uniformity of compression force across the plane of the compression paddle. Methods and apparatus to generate permanent direct records of compression force tests for quality assurance and medico-legal needs are also desired in the art.

SUMMARY OF THE INVENTION

The aforementioned long-felt needs are satisfied by methods and apparatus provided in accordance with the present invention. In preferred embodiments a film for use in radiographic imaging, adapted to measure performance of a compression device of a mammography unit which applies a compression force to a compression phantom positioned on a breast support platform of the mammography unit, comprising a radiographic image of the compression phantom after the compression force has been applied, and a compression force calibration pattern is provided.

In still further embodiments, methods of determining the magnitude of compression force applied by a mammography compression device to a compression phantom are provided in accordance with the present invention. The methods comprise the steps of positioning the compression phantom on a breast support platform of a mammography unit, moving a compression paddle of the mammography unit to apply a compression force to the compression phantom pressed against the breast support platform to change the shape of the compression phantom to produce a deformed compression phantom, radiographing the deformed compression phantom to create a latent image on a film positioned beyond the breast support platform, processing the film to develop a radiographic image of the deformed compression phantom, and determining the magnitude of the compression force used to deform the compression phantom, and determining the magnitude of the compression force used to deform the compression phantom to the extent shown on the radiographic image by comparing the image to a compression force calibration pattern.

In still further embodiments, methods of determining the uniformity of compression force applied by a mammography compression device are provided in accordance with the present invention. The methods comprise the steps of positioning two or more compression phantoms on a breast support platform of a mammography unit, between the breast support platform and a compression paddle of the mammography unit, moving the compression paddle to simultaneously apply a compression force to the compression phantoms to change the shapes of the compression phantoms to deformed compression phantoms, radiographing the deformed compression phantoms to produce latent images on a film positioned beyond the breast support platform, processing the film to develop radiographic images of the deformed compression phantoms, and determining the uniformity of the compression force used to change the shapes of the compression phantoms to the extent shown on the radiographic images by comparing the images to each' other and to a compression force calibration pattern.

In yet further embodiments, a compression phantom to measure a compression force applied by a compression device of a mammography unit to the compression phantom positioned on a breast support platform of the mammography unit, adapted with a compression force test means comprising a feature with a physical attribute that responds in a known reproducible manner to the application of the compression force, and a radiographic image recording the response of the feature to the compression force is provided.

In yet further embodiments, a compression phantom to measure a compression force applied by a compression device of a mammography unit to the compression phantom while radiographically imaging a breast phantom is provided.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which.

DETAILED DESCRIPTION OF PREFERRED EMBODIMENTS

This invention describes a method for validating that the compression force test was actually performed, and the magnitude of the compression force that was used in the test. In a preferred embodiment, the method consists of radiographing a modified bathroom type scale while a compression force is being applied to it by a mammography compression device, to create a radiographic image of a compression force indicator located in the scale.

Figure 1A:
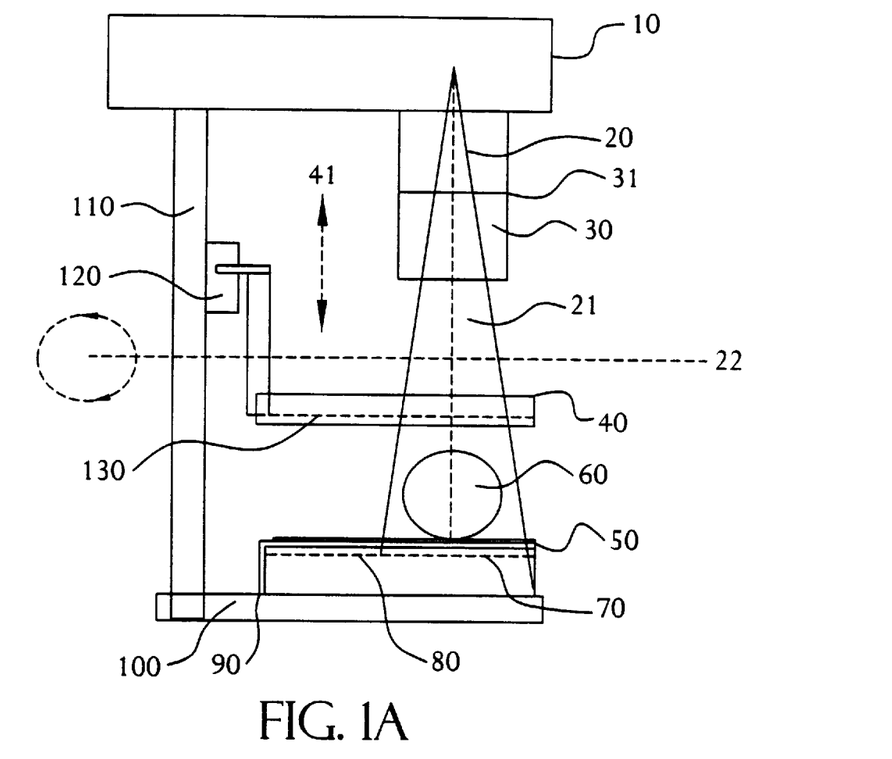
FIG. 1A is a schematic lateral view of the imaging and compression sections of a mammography unit, and a compression phantom in accordance with the present invention.

Referring now to the drawings wherein like reference numerals refer to like elements, in FIG. 1 A) an x-ray tube 10 of a mammography unit (not shown) produces an x-ray beam 20. The x-ray beam 20 passes through a cone 30 that contains a collimator 31 which limits the size and shape of the x-ray beam in any plane perpendicular to the axis 21 of the x-ray beam 20. The x-ray beam 20 also passes through a mammography compression device comprising a movable compression paddle 40 and a fixed breast support platform 50. The compression paddle 40 can be moved, either manually or remotely, in a line 41 parallel to the axis of the x-ray beam 21, in the direction of a compression phantom 60 positioned on the breast support platform 50. An x-ray film 70, in contact with an intensifying screen (not shown), for imaging the compression phantom 60, is contained within a cassette 80 that is positioned in cassette holder 90. Cassette holder 90 is rigidly supported by a platform 100 attached to a support column 110. The compression paddle is connected to support column 110 by a slideable connection 120. The plane 130 of the compression paddle 40 is parallel to the plane of the breast support platform 50.

In FIG. 1A) the axis of the x-ray beam is directed vertically downward. To facilitate angulation of the axis of the x-ray beam off the vertical while maintaining the relative positions of the numbered elements, x-ray tube 10 and platform 100 are ganged together by support column 110 which rotates clockwise or counterclockwise in a plane perpendicular to a line 22 located approximately midway between the x-ray tube 10 and platform 100.

Figure 1B:
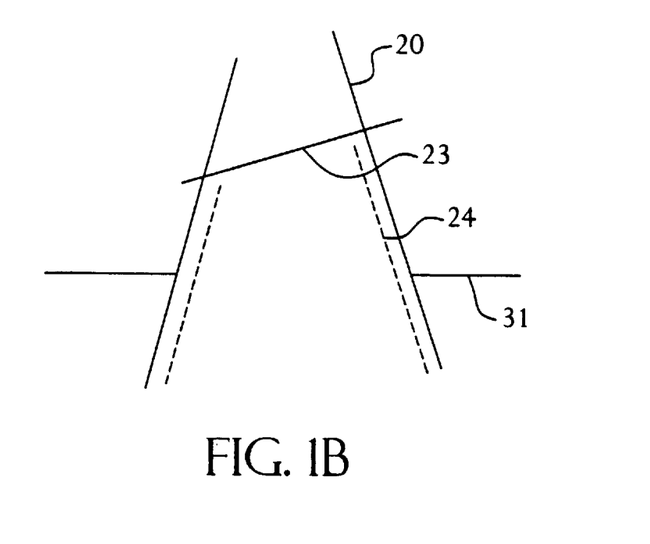
FIG. 1B is a section of FIG. 1A redrawn larger for clarity.

Referring to FIG. 1B), a mirror 23 positioned in x-ray beam 20 reflects visible light from an incandescent bulb (not shown) in collimator 31 as a light beam 24 in the same direction as the x-ray beam 20. Light beam 24 also passes through collimator 31 and cone 30. The action of mirror 23 and collimator 31 is to limit the size and shape of light beam 24 to be congruent with x-ray beam 20. Light beam 24 is used to facilitate proper positioning of compression phantom 60 in the x-ray field.

Figure 2:
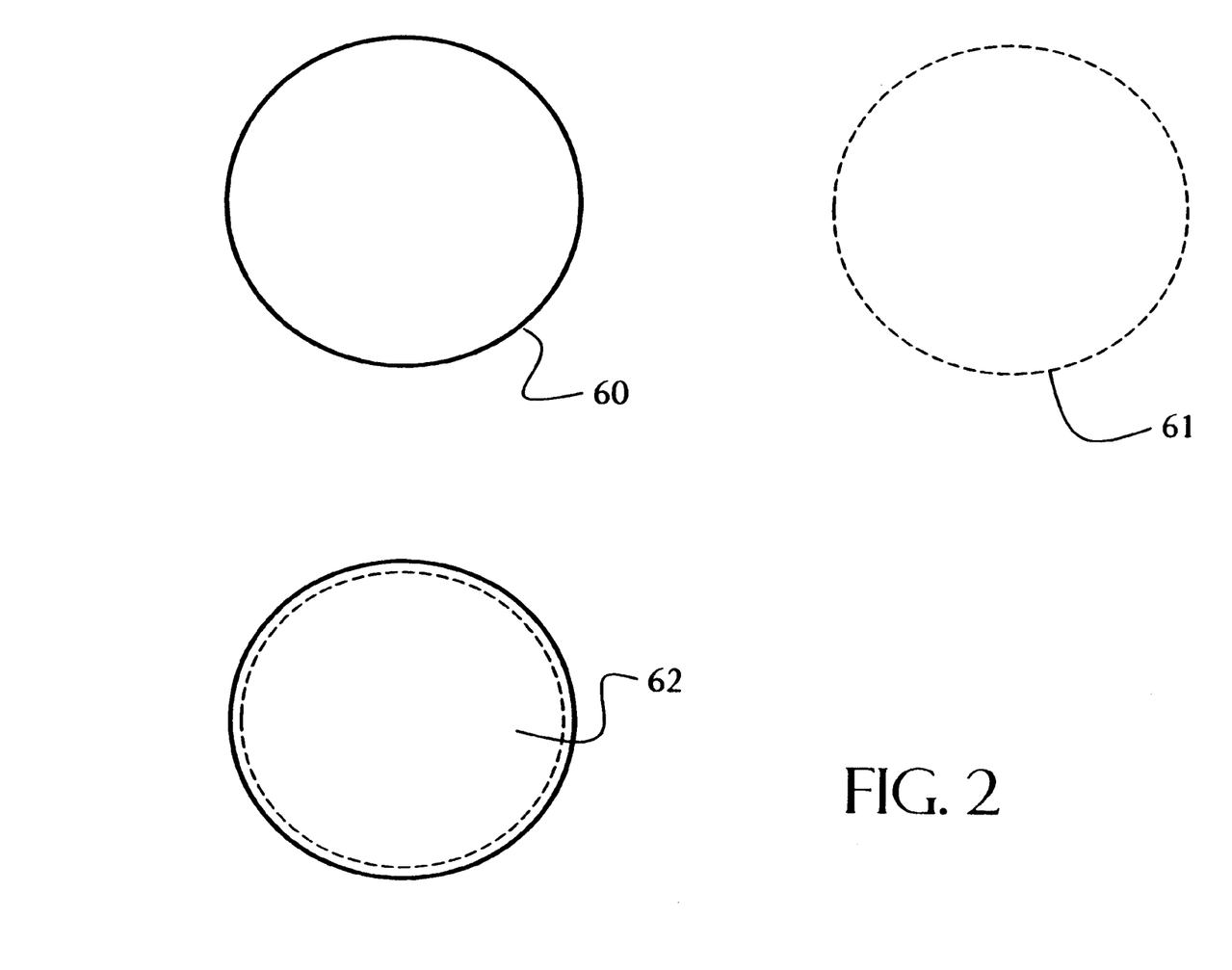
FIG. 2 is a schematic of a compression phantom in accordance with the present invention.

Referring to FIG. 2, compression phantom 60 is provided with feature 61 to measure a compression force exerted on compression phantom 60 by compression paddle 40. Feature 61 is comprised of material that is elastic and absorbs x-rays. In preferred embodiments feature 61 is also congruent with the surface of compression phantom 60. In preferred embodiments compression phantom 60 is configured in a first shape 62 comprising a hollow right circular cylinder.

Figure 3A:
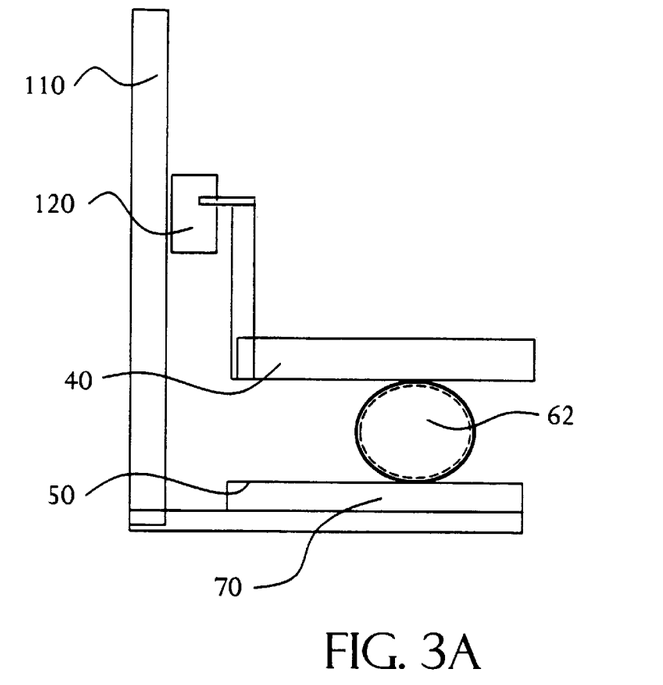
FIG. 3A and FIG. 3B are schematics of a compression phantom before and after the application of a compression force in accordance with the present invention.

Referring to FIG. 3A, to initiate a test of the mammography compression device, a compression phantom with first shape 62 is positioned on the breast support phantom 50 and compression paddle 40 is moved to make contact with the surface of the compression phantom. The compression phantom is light enough so that friction between its surface and the surface of compression paddle 40 is sufficient to retain the compression phantom in place even when breast support column 110 is rotated.

Figure 3B:
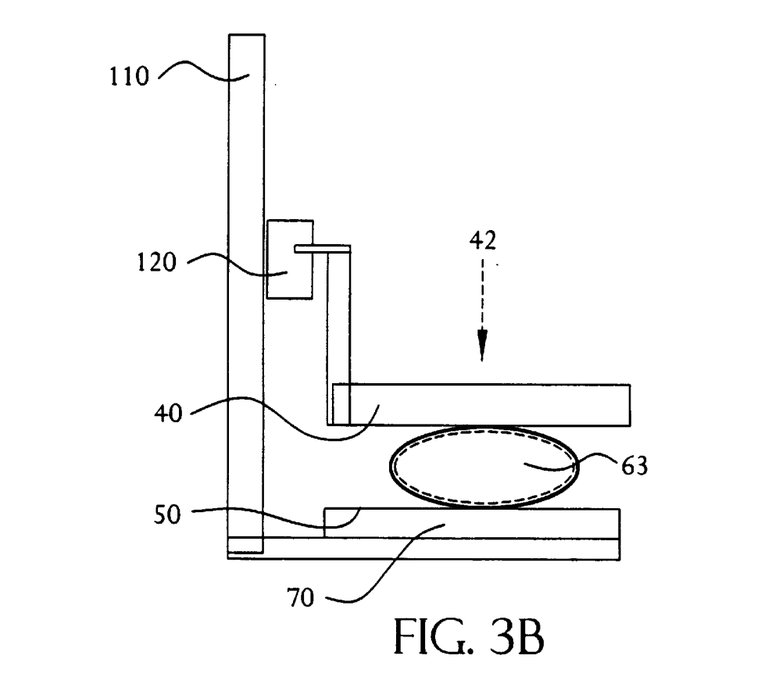

Referring to FIG. 3B a compression force 42 applied by the compression paddle 40 to a compression phantom configured in a first shape 62 as in FIG. 3A causes it to be physically changed into a second shape 63. The extent and direction of change depends on the physical attributes of the compression phantom, such as its size and composition, and also on the magnitude of the -applied compression force 42. By controlling the physical attributes of the compression phantom having first shape 62, the magnitude of the compression force 42 can be determined from measurements made on the compression phantom having second shape 63.

The elastic property of compression phantom 60 and feature 61 enable them to recover their original shapes after compression force 42 is released. Thus compression phantom 60 and feature 61 are reusable.

Figure 4:
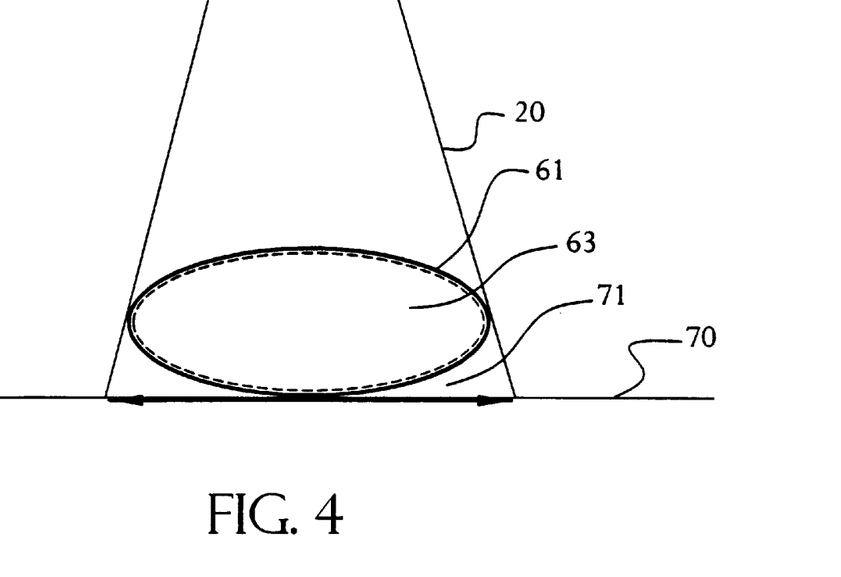
FIG. 4 is a schematic of a deformed compression phantom positioned for exposure to x-rays in accordance with the present invention.

Referring to FIG. 4, an x-ray exposure of the compression phantom having second shape 63 is made to create a latent image 71 of feature 61 on film 70 using x-ray beam 20. Since feature 61 absorbs x-rays, the size of latent image 71 in the x-y plane of film 70 depends on the extent of feature 61 in the plane that intercepts x-ray beam 20 during the x-ray exposure. Changes in the magnitude of compression force 42 applied to feature 61 produce changes in the extent of feature 61 and the size of latent image 71.

Figure 5:
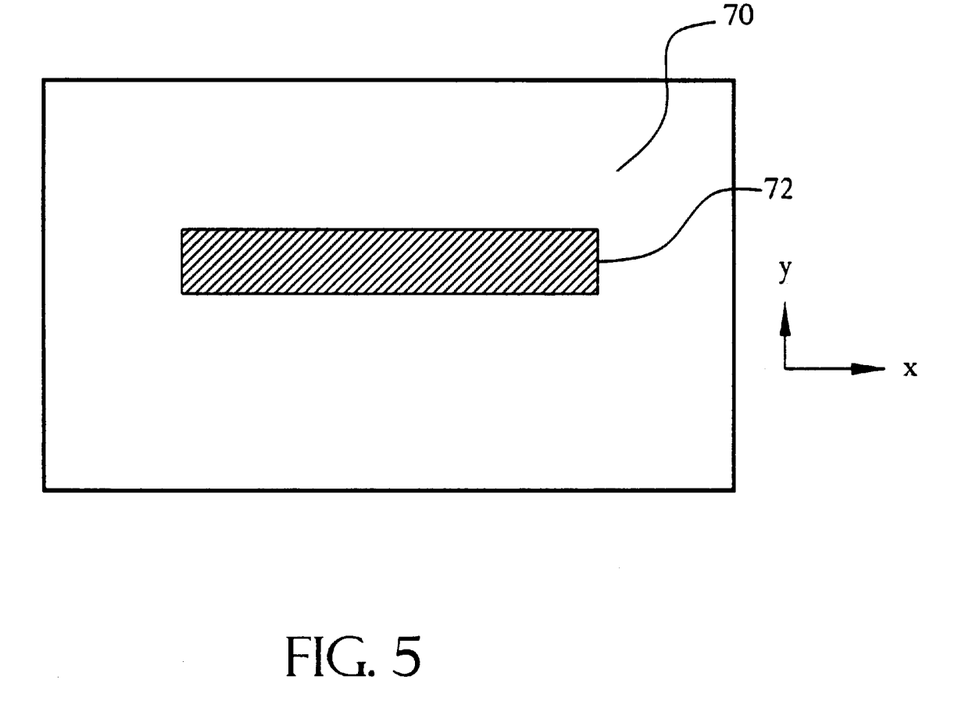
FIG. 5 is a schematic of a radiographic image of a deformed compression phantom in accordance with the present invention.

Referring to FIG. 5, after being exposed to x-rays, film 70 is processed to develop radiographic image 72 which records the two dimensional extent of feature 61 resulting from the action of compression force 42. For a compression phantom having elliptical shape 63 feature 61 projects as a rectangle.

A compression force measurement pattern is used in conjunction with radiographic image 72 to measure the magnitude of compression force 42. The compression force measurement pattern is pre-calibrated for use with compression phantoms of known construction and size.

It is well known in the art that the size of a radiographic image of an object located at a fixed distance from the plane of an imaging film is proportional to the perpendicular distance from the source of x-rays 20 to the plane of the film. For mammography units currently in use, this perpendicular distance can vary, typically over the range 45–65 cm. To account for this variation, the compression force measurement pattern is also calibrated to account for different source-to-film distances and different phantoms.

Figure 6A:
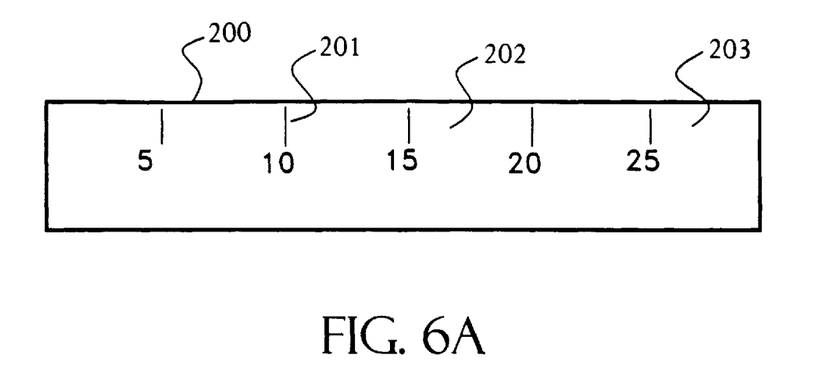
FIGS. 6A and 6B are compression force calibration patterns for measuring the magnitude of a compression force in accordance with the present invention.

Referring to FIG. 6A in preferred embodiments, compression force measurement pattern 200 consists of a line pattern 201 on a support material 202 and numeric markings 203 that are calibrated in terms of compression force. The markings read directly in units of applied compression force or indirectly against a look up table or graph. The magnitude of the compression force 42 is determined by noting the linear x and y extent of radiographic image 73 and comparing the size against the markings on the compression force measurement pattern.

Figure 6B:
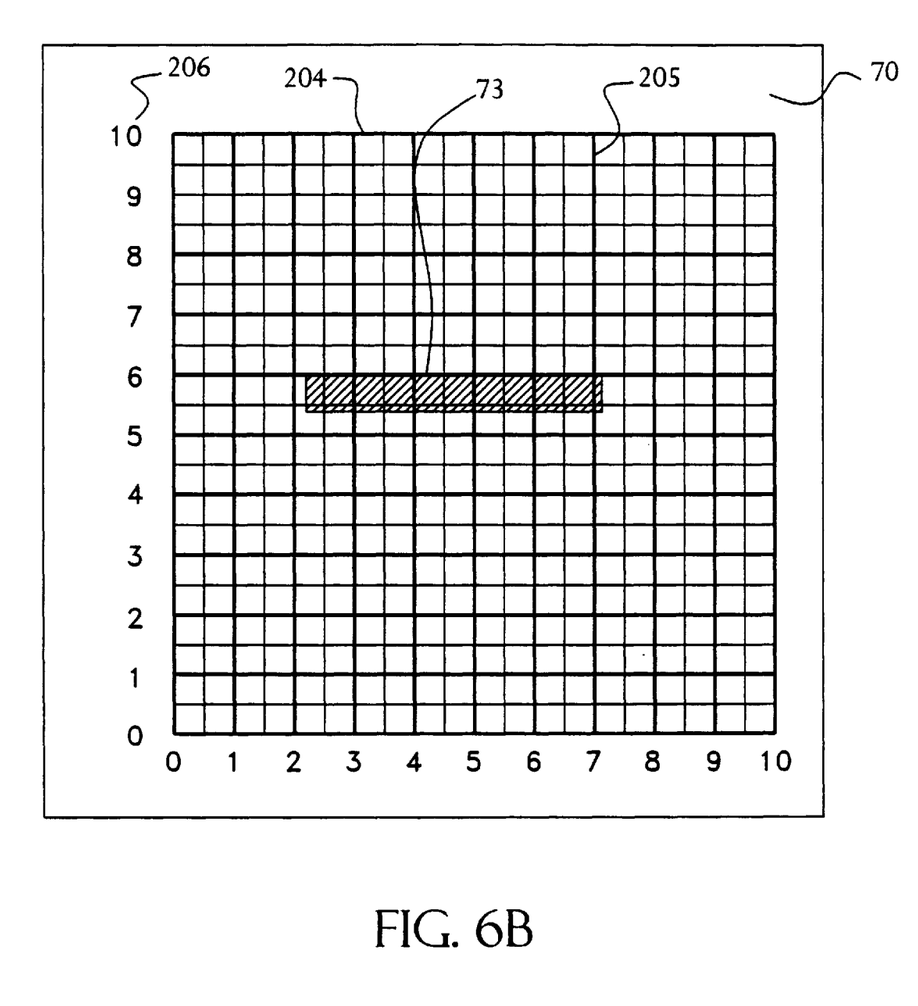

Referring to FIG. 6B in another embodiment a calibration force measurement pattern 204 is superimposed radiographically on radiographic image 73. A grid pattern 205 with numbered calibration markings 206, drawn on a transparent base (not shown), is inserted in cassette 80 between the intensifying screen and film 70 before the x-ray exposure is made. An image of the calibration force measurement pattern 204 is produced on film 70 by light emitted from the intensifying screen during x-ray exposure. The magnitude of compression force 42 is determined by noting the markings 206 where radiographic image 73 intercepts grid pattern 205.

Figure 7A:
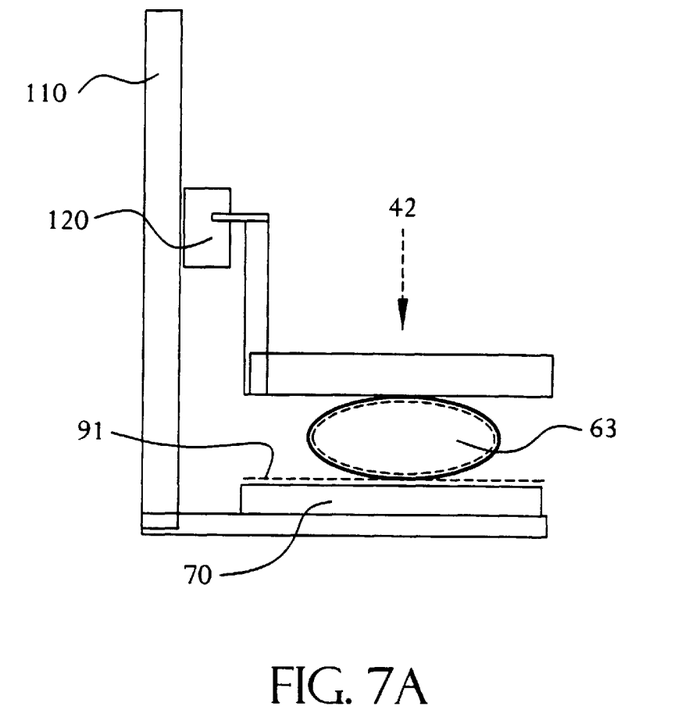
FIGS. 7A and 7B are diagrammatical views of a compression phantoms during the application of a compression force in accordance with the present invention, wherein one of the phantoms is provided with multiple objects of interest.

In another embodiment, shown in FIG. 7A, a compression force measurement pattern is produced radiographically on film 70 during the x-ray exposure of compression phantom 63. This pattern is the x-ray projection of a calibrated template having radiopaque numbered markings positioned at a predetermined x-ray source to template distance. The radiographic image of the markings are super-imposed on the radiographic image of the compression phantom. The magnitude of the compression force 42 is measured by comparing the size of radiographic image 73 against the radiographic image of the markings.

Figure 7B:
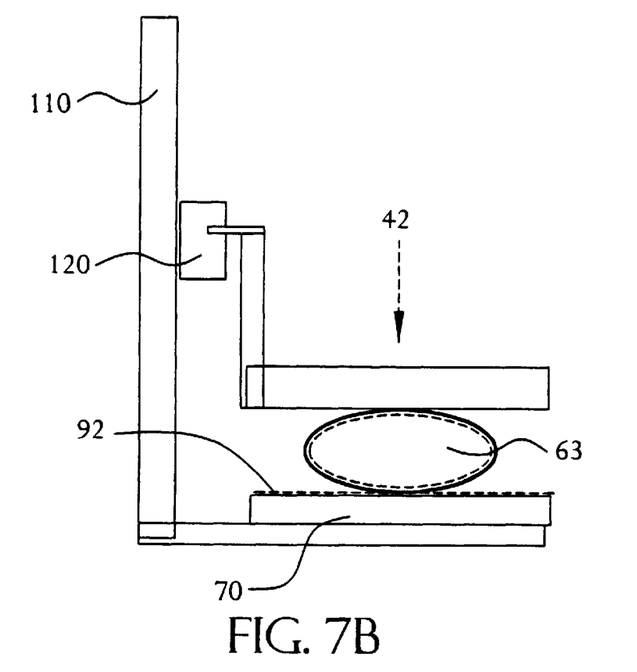

In yet another embodiment, shown in FIG. 7B, a calibrated compression force measurement pattern, comprising a visible line pattern with numbered markings, is provided to the surface of breast support platform 50. The magnitude of compression force 42 is measured visually by noting where the edge of the optical shadow of compression phantom 63, produced by compression phantom 63 intercepting light beam 24, projects on the calibrated markings.

In yet another embodiment a calibrated compression force measurement pattern, comprising an electronically stored pattern, is activated by sensors provided to the breast support platform 50. The sensors are responsive to visible light and/or x-rays and detect the edge of the optical and/or x-ray shadow of compression phantom 63. The magnitude of compression force 42 is determined electronically by comparing electrical signals from the activated sensors with the stored calibrated compression force measurement pattern.

While compression phantom 60 is configured as a hollow right circular cylinder. Other configurations are possible including solid configurations. In addition, the compression phantoms can be used with or incorporated into breast phantoms for use in mammography quality control programs.

Figure 8:
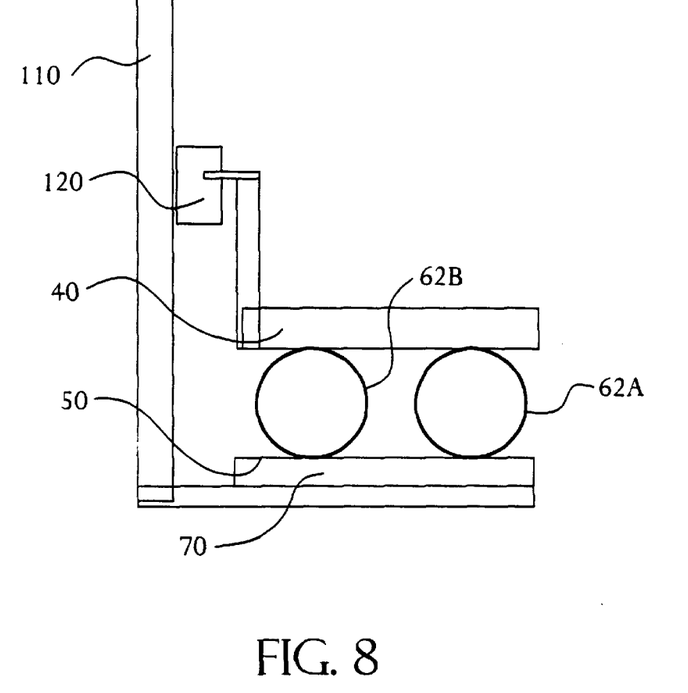
FIG. 8 is a diagrammatical view of multiple compression phantoms during the application of a compression force in accordance with the present invention.

In another embodiment, shown in FIG. 8, a compression force measurement pattern is produced radiographically on film 70 during the x-ray exposure of multiple compression phantoms 62A and 62B. The magnitude of the compression force 42 is again measured by comparing the size of radiographic image 73 against the radiographic image of the markings. This embodiment, however, permits one to determine whether the compression force is being applied uniformly throughout the compression paddle.

Figure 9:
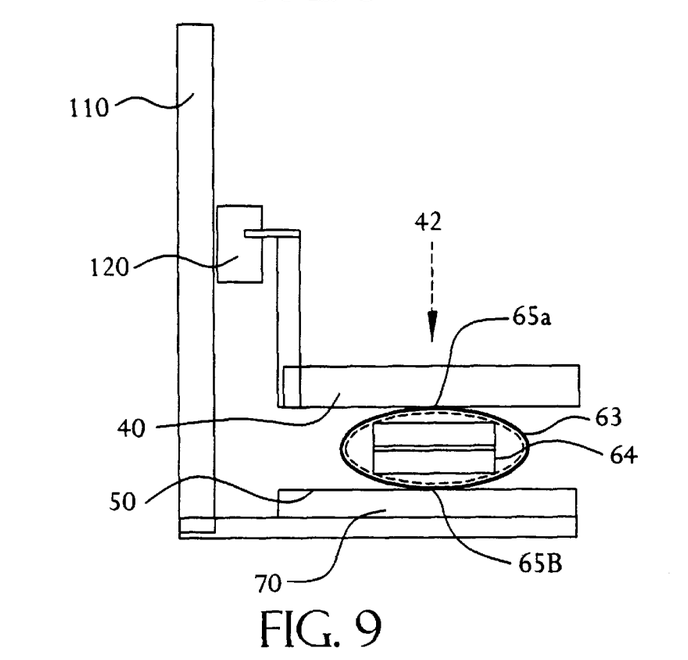
FIG. 9 is a diagrammatical view of an alternate embodiment of a compression phantom during the application of a compression force in accordance with the present invention.

In another embodiment, shown in FIG. 9, a compression force measurement pattern is produced radiographically on film 70 during the x-ray exposure of a compression phantom 63, which phantom includes a force indicating mechanism 64. The scale is a conventional type bathroom scale consisting of an outer, usually metal, casing that has a top U-shaped section and a bottom U-shaped section spaced apart by a support mechanism (not shown). The top section is molded to overhang the bottom section. The sections are connected by springs. When a force is applied to the scale, the top section moves toward the bottom section in the direction of the applied force. This motion activates a mechanism (not shown) in the casing that is connected to a force indicator. The indicator is usually a thin plastic or paper disc imprinted with numerical markings. The markings on the scale are visible through a thin plastic window in the top section. The applied force causes the disc to rotate in a plane parallel to the top surface, and the markings move opposite the window. The degree of rotation and the location of the markings relative to a pointer in the window are proportional to the magnitude of the compression force applied to the casing. The magnitude of a steady state force applied to the scale is determined by viewing the markings under the pointer. A written log of the compression test is made to comply with regulations.

Figure 10:
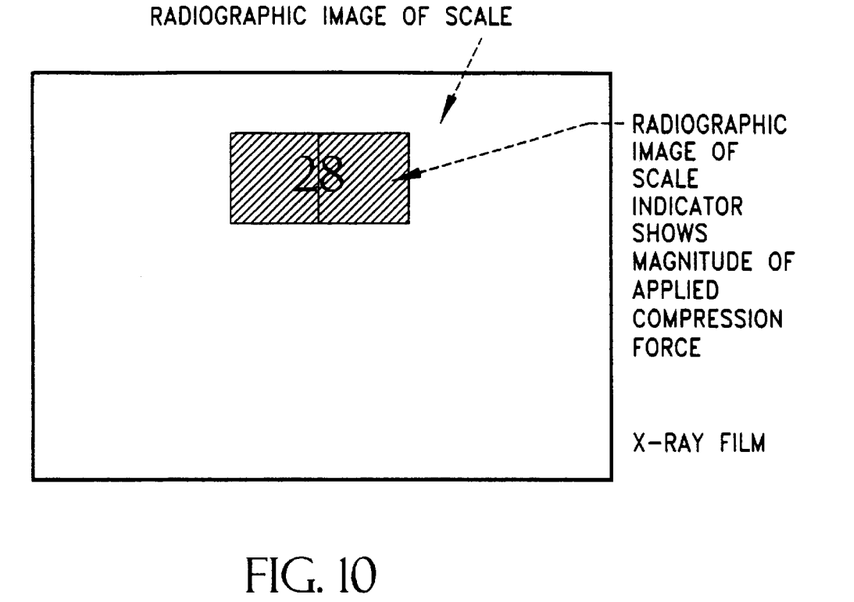
FIG. 10 is a top view of a radiographic image of a scale constructed in accordance with the invention.
Figure 11:
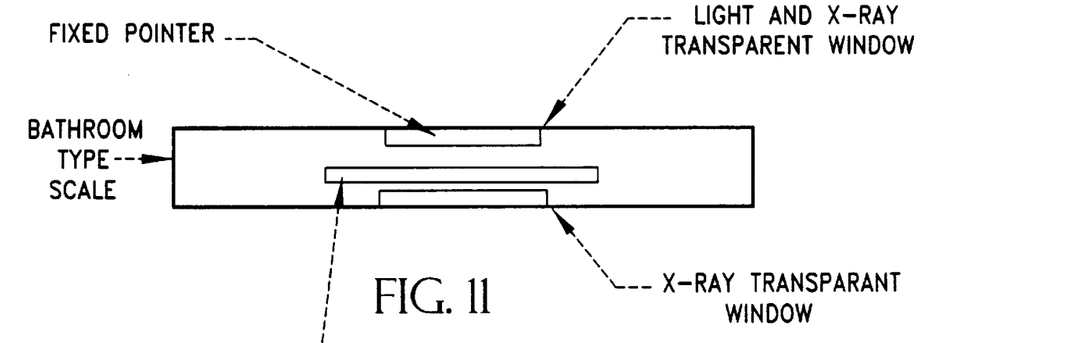
FIG. 11 is a side diagrammatic view of the scale imaged in FIG. 10.
Figure 12:
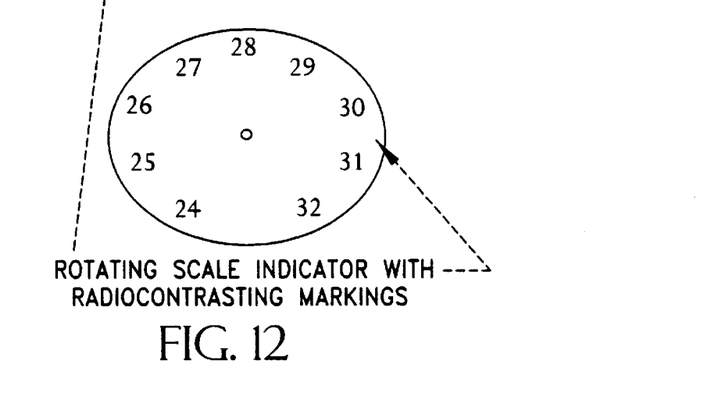
FIG. 12 is an isolated view of the scale indicator depicted in FIG. 11.

Mechanism 64 is a pressure activated rotating disk calibrated in terms of force. A force applied to the phantom activates the disk in a known manner, for example, the clockwise rotation exhibited in a bathroom scale. The final rotational position of the disk, indicating the applied force is located in an x-ray transparent aperture 65A and 65B formed in the phantom and is radiographed in that location. The aperture allows x-rays to pass un-absorbed except for their absorption by radio opaque markings on the disk. Force indicating markings present on the disk are formed from x-ray absorbing material. The magnitude of the compression force 42 is read directly from the radiographic image formed on the film. A scale modified to include x-ray transparent apertures 65A and 65B and radio contrasting markings could also be used for this purpose, as shown in FIGS. 10, 11 and 12.

In this invention the bottom section of the casing is adapted with a second window which is an x-ray transparent window, directly opposite the plastic window in the top surface. Thus both windows are x-ray transparent. In addition, the markings on the disc and the pointer under which the markings rotate are made of x-ray absorbent material.

For use, the modified scale is positioned on the breast support platform and a radiographic film in a regular screened cassette is positioned in the cassette holder. The section of the scale that contains the windows is positioned over the film and a compression force is applied to the scale by the compression paddle. The magnitude of the steady state applied compression force is recorded by exposing the scale to x-rays while the force is being applied. The x-rays pass through the windows to image the radiopaque scale markings and pointer on the film. A typical image is shown in Figure.

In another embodiment, padding is permanently applied to the top and bottoms surfaces of the casing to eliminate the need for the towels to protect the compression plate and support platform from damage during the use of the scale. In a preferred embodiment the padding is made of Velcro and sections of the Velcro are outfitted with Velcro straps to facilitate the positioning of the scale for measuring the compression force for any angulation of the x-ray unit.

This system provides an easy method for acquiring permanent records of mammography compression test results. These records can be used in lieu of hand written logs now used to show compliance with regulations.

While the invention has been described and illustrated with reference to specific embodiments, those skilled in the art will recognize that modifications and variations may be made without departing from the principles of the invention as described herein and set forth in the following claims.

What is claimed is:

1. Apparatus for use with a mammography unit to radiographically record the magnitude of a compression force applied to said scale by a compression device of said mammography unit, said apparatus comprising:

a casing with upper and lower sections, said sections having opposing x-ray transparent windows;

a force indicator located between said upper and lower sections, wherein said force indicator is a thin disc with numerical markings, said markings being radiopaque relative to the disc, and wherein said disc moves as a compression force is applied to said scale; and wherein the magnitude of said compression force is recorded by radiographing said force indicator to create a radiographic image of the numerical markings on a film.

2. Apparatus for determining the magnitude of a compression force applied by a mammography system to an object during x-ray imaging, said apparatus comprising:

a compression device for positioning within said system so that x-rays would be incident thereon and so that said compression force would be applied to said device, for measuring said compressive force, said compression device having an indicator member for indicating the amount of said compression force applied to said device, wherein said indicator member is formed from material which does not absorb x-rays; and x-ray absorbing material provided on said indicator member for indicating compressive force measured by said device;

wherein imaging of said compression device while compression force is applied by said system results in an image of said x-ray absorbing material on said indicator member and wherein the magnitude of said compression force is determined from the image of said x-ray absorbing material.

3. The apparatus of claim 2, wherein a portion of said device comprises x-ray transparent material, wherein said x-ray absorbing material is positioned in said device proximate said x-ray transparent material.

4. A compression force measuring apparatus for measuring compression force exerted by a compression paddle of a mammography unit on said apparatus when said apparatus is positioned on a mammography support platform of said mammography unit, said apparatus comprising a body to which said compression force is applied and a compression force indicator attached to said body, which indicator absorbs x-rays, wherein when said indicator is activated by said force and wherein when said apparatus is radiographed by said mammography unit a radiographic image of said indicator is produced indicative of the compression force being applied at the time of said radiograph.

5. The apparatus of claim 4, wherein a portion of said apparatus is constructed of material which does not absorb x-rays and wherein said indicator is located proximate said portion so that x-rays not absorbed by said apparatus may be absorbed by said indicator.

6. The apparatus of claim 5, wherein said indicator is constructed from material which does not absorb x-rays, further comprising x-ray absorbing material provided on said indicator, wherein said x-ray absorbing material is formed in a pattern on said indicator.

7. The apparatus of claim 6, wherein said pattern comprises a plurality of symbols, wherein each symbol indicates different amounts of said compression force.

8. The apparatus of claim 5, wherein said indicator comprises a disk formed from material which does not absorb x-rays, further comprising x-ray absorbing material provided on said indicator, wherein said x-ray absorbing material is formed as a pattern of numbers on said indicator.

* * * * *